US010451559B2

(12) United States Patent
Van Voorst et al.

(10) Patent No.: US 10,451,559 B2
(45) Date of Patent: Oct. 22, 2019

(54) ILLUMINATION SOURCE FOR AN INSPECTION APPARATUS, INSPECTION APPARATUS AND INSPECTION METHOD

(71) Applicant: ASML Netherlands B.V., Veldhoven (NL)

(72) Inventors: Peter Danny Van Voorst, Nijmegen (NL); Nan Lin, Eindhoven (NL); Sander Bas Roobol, Veldhoven (NL); Simon Gijsbert Josephus Mathijssen, Rosmalen (NL); Sietse Thijmen Van Der Post, Utrecht (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 16/102,178

(22) Filed: Aug. 13, 2018

(65) Prior Publication Data

US 2019/0003981 A1  Jan. 3, 2019

Related U.S. Application Data

(62) Division of application No. 15/683,216, filed on Aug. 22, 2017, now Pat. No. 10,330,606.

(30) Foreign Application Priority Data

Sep. 14, 2016 (EP) .................................... 16188816

(51) Int. Cl.
*G01N 21/88* (2006.01)
*G03F 7/20* (2006.01)
(Continued)

(52) U.S. Cl.
CPC ..... *G01N 21/8806* (2013.01); *G01N 21/9501* (2013.01); *G03F 7/7065* (2013.01);
(Continued)

(58) Field of Classification Search
CPC .......... G01N 21/8806; G01N 21/9501; G01N 2021/95676; G03F 7/70616; G03F 7/7065;
(Continued)

(56) References Cited

U.S. PATENT DOCUMENTS 3,754,195 A * 8/1973 Johnston, Jr. ......... H01S 3/0812
372/100
5,377,212 A * 12/1994 Tatsuno ................. G11B 7/127
359/328

(Continued)

FOREIGN PATENT DOCUMENTS

TW      2016-29469 A    8/2016

OTHER PUBLICATIONS

Kern Christian, "Extreme Nonlinear Optics with Spatially Controlled Light Fields," 2014, pp. 73-101.
(Continued)

*Primary Examiner* — Sang H Nguyen
(74) *Attorney, Agent, or Firm* — Sterne, Kessler, Goldstein & Fox P.L.L.C.

(57) ABSTRACT

Disclosed is an inspection apparatus and associated method for measuring a target structure on a substrate. The inspection apparatus comprises an illumination source for generating measurement radiation; an optical arrangement for focusing the measurement radiation onto said target structure; and a compensatory optical device. The compensatory optical device may comprise an SLM operable to spatially modulate the wavefront of the measurement radiation so as to compensate for a non-uniform manufacturing defect in said optical arrangement. In alternative embodiments, the compensatory optical device may be located in the beam of measurement radiation, or in the beam of pump radiation used to generate high harmonic radiation in a HHG source.

(Continued)

Where located in the beam of pump radiation, the compensatory optical device may be used to correct pointing errors, or impart a desired profile or varying illumination pattern in a beam of the measurement radiation.

13 Claims, 6 Drawing Sheets

(51) Int. Cl.
*G01N 21/95* (2006.01)
*H05G 2/00* (2006.01)
*G01N 21/956* (2006.01)

(52) U.S. Cl.
CPC .......... *G03F 7/70616* (2013.01); *H05G 2/00* (2013.01); *G01N 2021/95676* (2013.01); *H05G 2/008* (2013.01)

(58) Field of Classification Search
CPC ........ H05G 2/001; H05G 2/003; H05G 2/008; G01F 1/353; G02F 1/3544
See application file for complete search history.

(56) References Cited

U.S. PATENT DOCUMENTS

| | | | |
|---|---|---|---|
| 6,774,991 B1 | 8/2004 | Danko | |
| 2002/0172235 A1* | 11/2002 | Chang | G02F 1/353 372/5 |
| 2003/0142910 A1* | 7/2003 | Behringer | G02B 6/4204 385/33 |
| 2004/0012775 A1 | 1/2004 | Kinney et al. | |
| 2005/0152426 A1* | 7/2005 | Dell'Acqua | H01S 3/0941 372/69 |
| 2005/0219518 A1 | 10/2005 | Korngut et al. | |
| 2005/0243390 A1 | 11/2005 | Tejnil | |
| 2005/0244164 A1* | 11/2005 | Miyashita | H04B 10/25253 398/147 |
| 2006/0001855 A1* | 1/2006 | Lof | G03F 7/70275 355/69 |
| 2006/0066855 A1 | 3/2006 | Boef et al. | |
| 2008/0137696 A1* | 6/2008 | Zhang | H01S 4/00 372/22 |
| 2008/0144672 A1* | 6/2008 | Cohen | G02F 1/353 372/5 |
| 2011/0013653 A1* | 1/2011 | Krausz | G02F 1/3501 372/22 |
| 2011/0075151 A1 | 3/2011 | Jeong | |
| 2011/0102753 A1 | 5/2011 | Van De Kerkhof et al. | |
| 2012/0044470 A1 | 2/2012 | Smilde et al. | |
| 2014/0071421 A1 | 3/2014 | De Jager et al. | |
| 2014/0375981 A1 | 12/2014 | Wang et al. | |
| 2015/0049457 A1* | 2/2015 | Kroell | G01N 21/8806 362/84 |
| 2015/0098126 A1* | 4/2015 | Keller | G02B 21/0076 359/385 |
| 2016/0091422 A1 | 3/2016 | Van Der Zouw | |
| 2016/0161245 A1 | 6/2016 | Eu et al. | |
| 2016/0282280 A1* | 9/2016 | Foad | G01N 21/95 |
| 2018/0073992 A1 | 3/2018 | Van Voorst et al. | |

OTHER PUBLICATIONS

Mimura et al., "Breaking the 10nm barrier in hard-X-ray focusing," Nature Physics, vol. 6, Feb. 2009; pp. 122-125.

Eyring et al., "Improving high-order harmonic yield using wavefront-controlled ultrashort laser pulses," Optical Society of America, Optics Express, vol. 20, No. 5, 2012; pp. 5601-5606.

Gariepy et al., "Creating High-Harmonic Beams with Controlled Orbital Angular Momentum," American Physical Society, Physical Review Letters, vol. 113, 2014; pp. 1-5.

Zurch M.W., "High-Resolution Extreme Ultraviolet Microscopy," Springer Theses, 2015; pp. 1-6.

Fujino et al., "Extreme ultraviolet mask observations using a coherent extreme ultraviolet scatterometry microscope with a high-harmonic-generation source," The Japanese Society of Applied Physics, Japanese Journal of Applied Physics, vol. 54, 2015; pp. 1-6.

Walter et al., "Adaptive spatial control of fiber modes and their excitation for high-harmonic generation," Optical society of America, Optics Express, Volc. 14, No. 8, 2006; pp. 3433-3442.

Ohsuka et al., "Laboratory-size three-dimensional x-ray microscope with Wolter type I mirror optics and an electron-impact water window x-ray source," Review of Scientific Instruments, vol. 85, No. 093701, 2014; pp. 1-5.

International Search Report and Written Opinion of the International Searching Authority directed to related International Patent Application No. PCT/EP2017/069506, dated Jan. 2, 2018; 17 pages.

Non-Final Office Action for U.S. Appl. No. 15/683,216, dated Oct. 18, 2018; 11 pages.

* cited by examiner

ILLUMINATION SOURCE FOR AN INSPECTION APPARATUS, INSPECTION APPARATUS AND INSPECTION METHOD

CROSS REFERENCE TO RELATED APPLICATIONS

This application incorporates by reference in their entireties European Patent Application No. 16188816.9, filed Sep. 14, 2016 and U.S. patent application Ser. No. 15/683,216, filed Aug. 22, 2017.

FIELD

The present invention relates to a lithographic apparatus and a method for performing a measurement. In particular, it relates to an inspection apparatus comprised in a lithographic apparatus, and in particular its illumination source, as well as a method for performing a measurement therewith.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Multiple layers, each having a particular pattern and material composition, are applied to define functional devices and interconnections of the finished product.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field.

Examples of known scatterometers often rely on provision of dedicated metrology targets. For example, a method may require a target in the form of a simple grating that is large enough that a measurement beam generates a spot that is smaller than the grating (i.e., the grating is underfilled). In so-called reconstruction methods, properties of the grating can be calculated by simulating interaction of scattered radiation (throughout this text, scattered radiation may include radiation which is scattered, reflected or diffracted by the target, depending on the metrology scheme used) with a mathematical model of the target structure. Parameters of the model are adjusted until the simulated interaction produces a diffraction pattern similar to that observed from the real target.

In addition to measurement of feature shapes by reconstruction, diffraction-based overlay can be measured using such apparatus, as described in published patent application US2006066855A1. Diffraction-based overlay metrology using dark-field imaging of the diffraction orders enables overlay measurements on smaller targets. These targets can be smaller than the illumination spot and may be surrounded by product structures on a wafer. Examples of dark field imaging metrology can be found in numerous published patent applications, such as for example US2011102753A1 and US20120044470A. Multiple gratings can be measured in one image, using a composite grating target. The known scatterometers tend to use light in the visible or near-IR wave range, which requires the pitch of the grating to be much coarser than the actual product structures whose properties are actually of interest. Such product features may be defined using deep ultraviolet (DUV) or extreme ultraviolet (EUV) radiation having far shorter wavelengths. Unfortunately, such wavelengths are not normally available or usable for metrology.

On the other hand, the dimensions of modern product structures are so small that they cannot be imaged by optical metrology techniques. Small features include for example those formed by multiple patterning processes, and/or pitch-multiplication. Hence, targets used for high-volume metrology often use features that are much larger than the products whose overlay errors or critical dimensions are the property of interest. The measurement results are only indirectly related to the dimensions of the real product structures, and may be inaccurate because the metrology target does not suffer the same distortions under optical projection in the lithographic apparatus, and/or different processing in other steps of the manufacturing process. While scanning electron microscopy (SEM) is able to resolve these modern product structures directly, SEM is much more time consuming than optical measurements. Moreover, electrons are not able to penetrate through thick process layers, which makes them less suitable for metrology applications. Other techniques, such as measuring electrical properties using contact pads is also known, but it provides only indirect evidence of the true product structure.

By decreasing the wavelength of the radiation used during metrology (i.e. moving towards the "soft X-ray" (SXR) wavelength spectrum), it is possible to resolve smaller structures, to increase sensitivity to structural variations of the structures and/or penetrate further into the product structures, Soft X-ray radiation may be defined as radiation having a wavelength within the 1 nm to 50 nm range. An issue with the use of soft X-ray radiation is that it may result in increased blurring of the measurement spot on the target area. This is due to the "slope error" of the reflective optics which focus the measurement radiation onto a spot on the target area. The slope error is a particular problem in the soft X-ray regime because surface flatness of an optical surface is described in terms of wavelength of the radiation incident on the surface; it is much more difficult to achieve acceptable surface flatness for smaller wavelengths. The blurring of the measurement spot is an important issue, as it is important that the illumination only illuminates the target area and not its surrounding environment. Other issues with the measurement spot include its profile and the accuracy of its positioning, for example.

SUMMARY

It would be desirable to improve measurement spot focusing in metrology applications.

Alternatively, or in addition, it would be desirable to improve control of one or more parameters of the measurement radiation in an improved manner.

According to a first aspect of the present invention, there is provided an inspection apparatus for measuring a target structure on a substrate, comprising: an illumination source for generating measurement radiation; an optical arrangement for focusing the measurement radiation onto said target structure, the optical arrangement comprising at least one optical element being arranged to receive said measurement radiation at a grazing incidence; and a compensatory optical device operable to spatially modulate the wavefront of the measurement radiation so as to compensate for a non-uniform manufacturing defect in said optical arrangement.

According to a second aspect of the present invention, there is provided a method of measuring a target structure on a substrate comprising: spatially modulating the wavefront of measurement radiation to compensate for a non-uniform manufacturing defect in an optical arrangement comprising one or more optical elements; focusing the measurement radiation onto said target structure using said optical arrangement such that at least one optical element receives the measurement radiation at a grazing incidence, thereby illuminating the target structure with the measurement radiation; detecting scattered radiation resulting from the illumination of the target with the measurement radiation; and processing the detected scattered radiation to determine a measurement value relating to said target structure.

According to a third aspect of the present invention, there is provided an illumination source for generating high harmonic radiation, comprising: a high harmonic generation medium; a pump radiation source which emits a beam of pump radiation for exciting said high harmonic generation medium to generate said high harmonic radiation; and a compensatory optical device operable to spatially modulate the wavefront of the beam of pump radiation prior to it exciting said high harmonic generation medium.

Further aspects, features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant arts) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
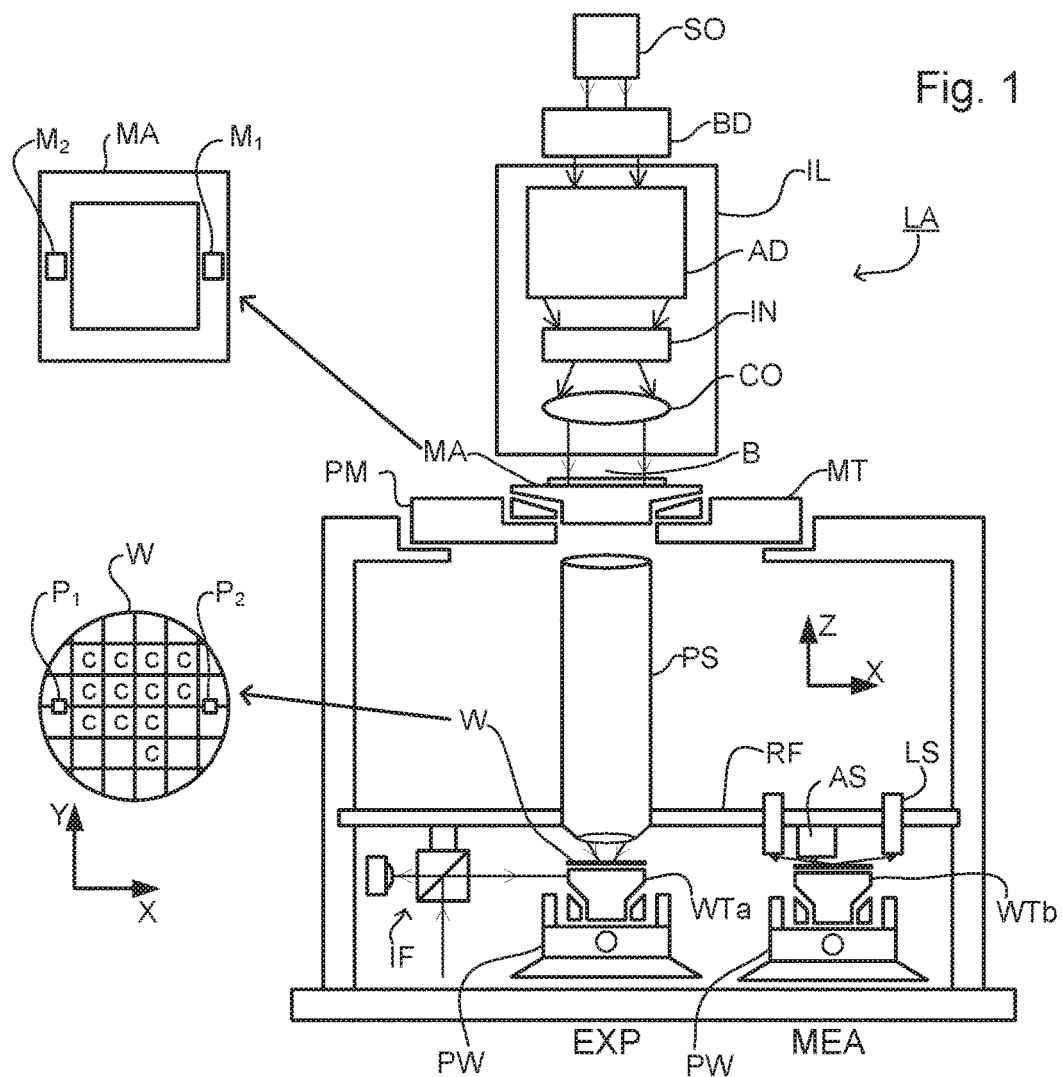
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV or EUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support MT may be a frame or a table, for example, which may be fixed or movable as required. The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL, may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment mark may also be included within dies, in amongst the device features, in which case it is desirable that the markers be as small as possible and not require any different imaging or process conditions than adjacent features. The alignment system, which detects the alignment markers is described further below.

The depicted apparatus could be used in a variety of modes. In a scan mode, the patterning device support (e.g., mask table) MT and the substrate table WT are scanned synchronously while a pattern imparted to the radiation beam is projected onto a target portion C a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

Figure 2:
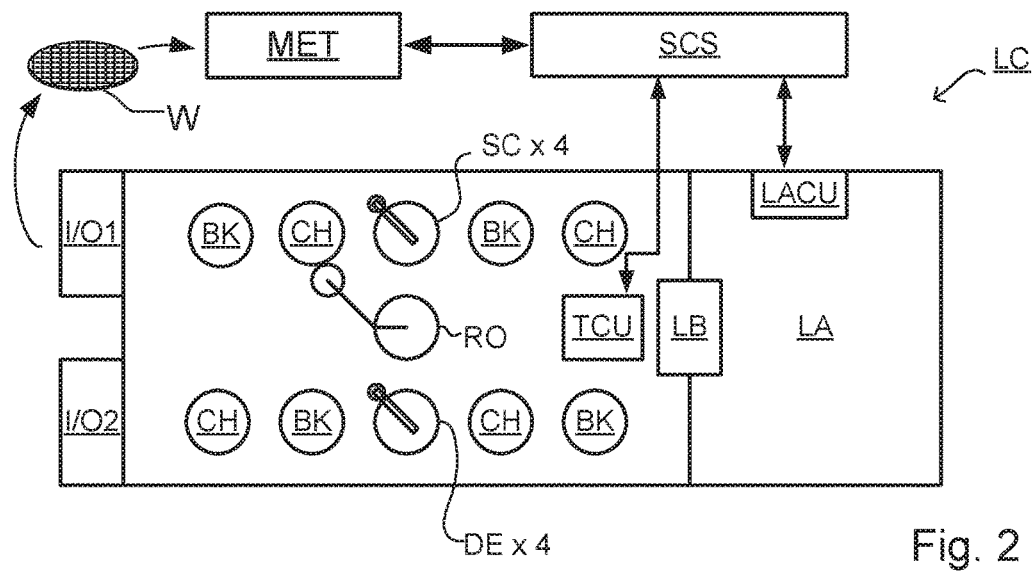
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

The substrates processed by the track are then transferred to other processing tools for etching and other chemical or physical treatments within the device manufacturing process. In some instances, metrology may be performed on substrates after such etching or chemical/physical treatment steps.

The lithographic apparatus control unit LACU controls all the movements and measurements of the various actuators and sensors described. LACU also includes signal processing and data processing capacity to implement desired calculations relevant to the operation of the apparatus. In the terminology of the introduction and claims, the combination of these processing and control functions referred to simply as the "controller". In practice, control unit LACU will be realized as a system of many sub-units, each handling the real-time data acquisition, processing and control of a subsystem or component within the apparatus. For example, one processing subsystem may be dedicated to servo control of the substrate positioner PW. Separate units may even handle coarse and fine actuators, or different axes. Another unit might be dedicated to the readout of the position sensor IF. Overall control of the apparatus may be controlled by a central processing unit, communicating with these subsystems processing units, with operators and with other apparatuses involved in the lithographic manufacturing process.

Figure 3A:
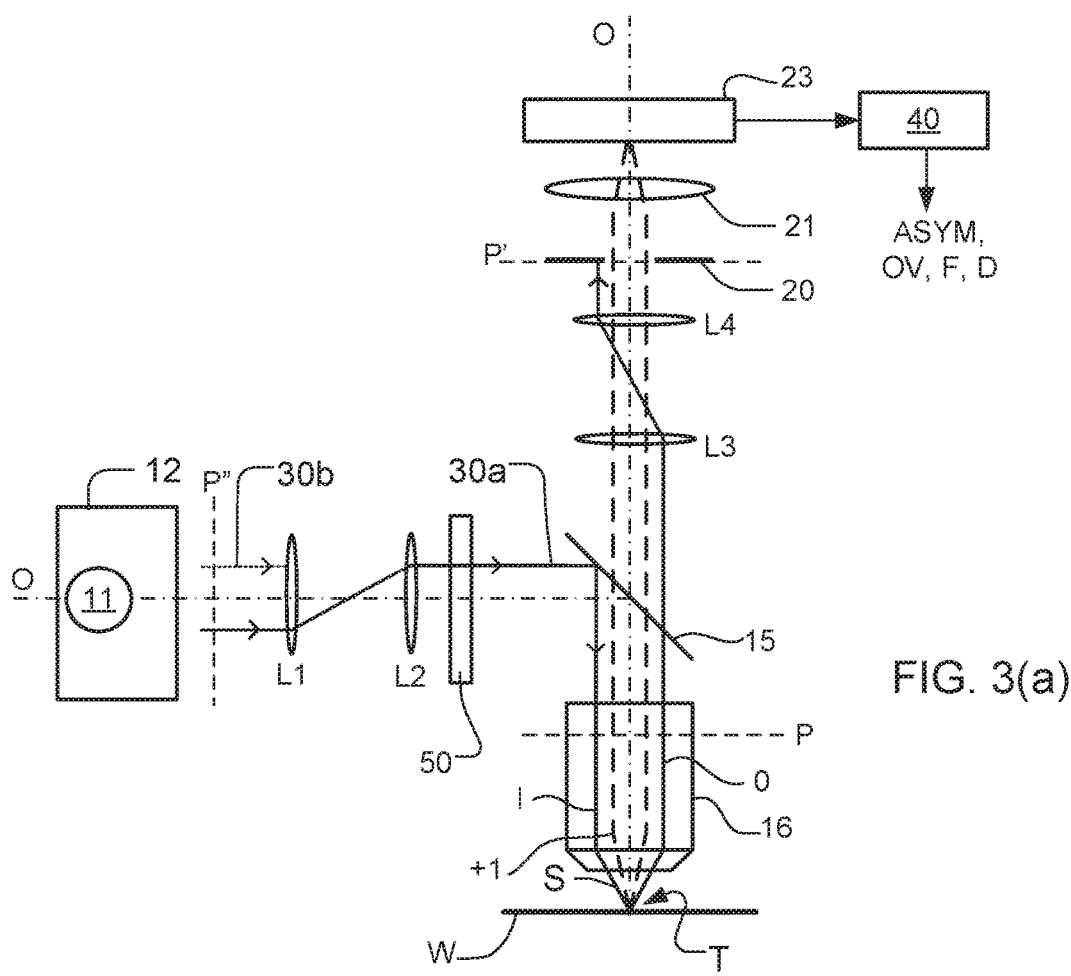
FIGS. 3(a)-3(b) illustrate schematically an inspection apparatus according to an embodiment of the invention adapted to perform a known dark-field imaging inspection methods.

FIG. 3(a) shows schematically the key elements of an inspection apparatus implementing so-called dark field imaging metrology. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating structure T and diffracted rays are illustrated in more detail in FIG. 3(b).

As described in the prior applications cited in the introduction, the dark-field-imaging apparatus of FIG. 3(a) may be part of a multi-purpose angle-resolved scatterometer that may be used instead of or in addition to a spectroscopic scatterometer. In this type of inspection apparatus, radiation emitted by a radiation source 11 is conditioned by an illumination system 12. For example, illumination system 12 may include a collimating lens system, a color filter, a polarizer and an aperture device. The conditioned radiation follows an illumination path, via lenses L1, L2, and in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures over 1 if desired. The multi-purpose scatterometer may have two or more measurement branches. Additionally, further optical systems and branches will be included in a practical apparatus, for example to collect reference radiation for intensity normalization, for coarse imaging of capture targets, for focusing and so forth. Details of these can be found in the prior publications mentioned above. For the purposes of the present disclosure, only the measurement branch of interest for the dark-filed imaging metrology is illustrated and described in detail.

In the collection path for dark-field imaging comprising lenses L2, L4, imaging optical system 21 forms an image of the target on the substrate W on sensor 23 (e.g, a CCD or CMOS sensor). An aperture stop 20 is provided in a plane P' in the collection path. Plane P' is a plane conjugate to a pupil plane P of objective lens 16. Pupil plane P may be the plane a distance f2 away from lens L2 and a distance f3 away from lens L3, where f2 and f3 are the focal lengths of lenses L2 and L3 respectively. Aperture stop 20 may also be called a pupil stop. Aperture stop 20 can take different forms, just as the illumination aperture can take different forms. The aperture stop 20, in combination with the effective aperture of lens 16, determines what portion of the scattered radiation is used to produce the image on sensor 23. Typically, aperture stop 20 functions to block the zeroth order diffracted beam so that the image of the target formed on sensor 23 is formed only from the first order beam(s). In an example where both first order beams are combined to form an image, this would be the so-called dark field image, equivalent to dark-field microscopy. In the present application, however, only one of the first orders is imaged at a time, as explained below. The images captured by sensor 23 are output to image processor and controller 40, the function of which will depend on the particular type of measurements being performed. For the present purpose, measurements of asymmetry of the target structure are performed. Asymmetry measurements can be combined with knowledge of the target structures to obtain measurements of performance parameters of lithographic process used to form them. Performance parameters that can be measured in this way include for example overlay, focus and dose.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. Each of these gratings is an example of a target structure whose properties may be investigated using the inspection apparatus.

The various components of illumination system 12 can be adjustable to implement different metrology 'recipes' within the same apparatus. In addition to selecting wavelength (color) and polarization as characteristics of the particular, illumination system 12 can be adjusted to implement different illumination profiles. Because plane P" is conjugate with pupil plane P of objective lens 16 and the plane of the detector 19, an illumination profile in plane P" defines the angular distribution of light incident on substrate W in spot S. To implement different illumination profiles, an aperture device can be provided in the illumination path. The aperture device may comprise different apertures mounted on a movable slide or wheel. If may alternatively comprise a programmable spatial light modulator. As a further alternative, optical fibers may be disposed at different location in the plane P" and used selectively to deliver light or not deliver light at their respective locations. These variants are all discussed and exemplified in the documents cited above.

In a first example illumination mode, rays 30a are provided so that the angle: of incidence is as shown at 'I' and the path of the zero order ray reflected by target T is labeled '0' (not to be confused with optical axis 'O'). In a second illumination mode, rays 30b can be provided, in which case the angles of incidence and reflection will be swapped. Both of these illumination modes will be recognized as off-axis illumination modes. Many different illumination modes can be implemented for different purposes.

Figure 3B:
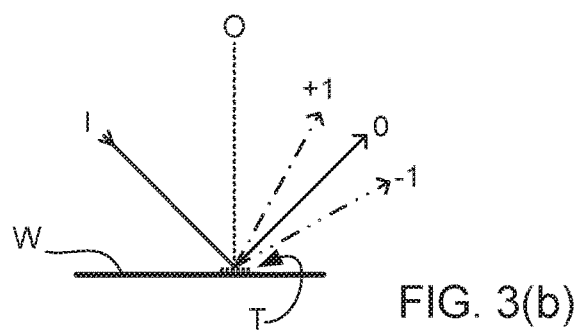

As shown in more detail in FIG. 3(b), target grating T as an example of a target structure is placed with substrate W normal to the optical axis O of objective lens 16. In the case of an off-axis illumination profile, a ray of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the beam of illuminating rays 30a has a finite width (necessary to admit a useful quantity of light), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

Referring also to FIG. 3(a), under the first illumination mode with rays 30a, +1 order diffracted rays from the target grating will enter the objective lens 16 and contribute to the image recorded at sensor 23. When the second illumination mode is used, rays 30b are incident at an angle opposite to rays 30b, and so the −1 order diffracted rays enter the objective and contribute to the image. Aperture stop 20 blocks the zeroth order radiation when using off-axis illumination. As described in the prior publications, illumination modes can be defined with off-axis illumination in X and Y directions.

By comparing images of the target grating under these different illumination modes, asymmetry measurements can be obtained. Alternatively, asymmetry measurements could be obtained by keeping the same illumination mode, but rotating the target. While off-axis illumination is shown, on-axis illumination of the targets may instead be used and a modified, off-axis aperture 20 could be used to pass substantially only one first order of diffracted light to the sensor. In a further example, prisms are used in place of aperture stop 20 which have the effect of diverting the +1 and −1 orders to different locations on sensor 23 so that they can be detected and compared without the need for two sequential image capture steps. This technique, is disclosed in the above-mentioned published patent application US2011102753A1, the contents of which are hereby incorporated by reference. 2nd, 3rd and higher order beams (not shown in FIG. 3) can be used in measurements, instead of or in addition to the first order beams. As a further variation, the off-axis illumination mode can be kept constant, while the target itself is rotated 180 degrees beneath objective lens 16 to capture images using the opposite diffraction orders.

The above techniques are typically performed using radiation with a visible wavelength. As such, the scatterometry targets have a pitch that is larger than that of the product structures on the substrate. As an example, a scatterometry target may have a target grating pitch measured in microns (μm), whereas product structures on the same substrate may have a pitch measured in nanometers (nm).

This difference in pitch induces an offset between the measured overlay and the actual overlay on the product structures. The offset is at least partly due to optical projection distortions in the lithographic apparatus and/or different processing in other steps of the manufacturing process. Presently, the offset comprises a significant contribution to the overall measured overlay. Reducing or eliminating it will therefore improve overall overlay performance.

Metrology tools may be developed which use sources that emit radiation in "soft X-ray" or EUV range, for example having wavelengths between 2 nm and 50 nm, or between 0.1 nm and 100 nm, or in between 1 nm and 100 nm, or in between 5 nm and 50 nm, or in between 10 nm and 20 nm. The emitted spectrum may comprise the wavelength of 13.5 nm. Examples of such sources include Discharge Produced Plasma sources, Laser Produced Plasma Sources or High-order Harmonic Generation (HHG) sources. HHG sources are known to be able to provide large flux of collimated photons (high luminance) in the emitted light.

HHG sources used in metrology applications are illustrated and further described in the European patent applications EP152020301, EP16168237, EP16167512, which are hereby incorporated in their entirety by reference. In metrology applications, such HHG sources may be used (for example) in normal incidence, very close to normal incidence (e.g., within 10 degrees from normal), at a grazing incidence (e.g., within 20 degrees from surface), at an arbitrary angle or at multiple angles (to obtain more measurement information in a single capture).

To perform a diffraction-based measurement, e.g. to determine overlay error or critical dimension, target structures should be preferably "underfilled" (i.e. the spot diameter is smaller than the size of the target). If the spot diameter is increased, the size of the target must therefore also be increased proportionally. Larger targets take up more space on the surface of a substrate, which is undesirable in a production environment since it, for example, increases the per-product manufacturing costs. While it is desirable to maintain targets as small as possible, it is also important that the measurement radiation only illuminates the target, and not its surrounding environment. By way of example, 99.99% of incoming measurement radiation should be incident on the target structure during a measurement. To achieve this with small targets, it is important that the measurement spot size (the size of the target area illuminated by the measurement radiation) is well controlled and properly focused on the target.

The optics used to focus the measurement radiation on a target structure will not be perfect. A particular issue is the "slope error" resulting from medium spatial-frequency modulations of the surface due to manufacturing imperfections. The result of the slope error is that focusing will not be perfect and the measurement spot will be subject to some blurring, for example a blur ring or halo may form around the main focused spot. This can result in some measurement radiation missing the target structure and encroaching into the surrounding environment. These medium spatial-frequency modulations are in contrast to high spatial-frequency modulations (i.e., surface roughness) which does not affect spot quality, only intensity due to radiation loss; and to low spatial-frequency modulations such as surface errors which induce aberrations. It is possible to optimize design of the optics to minimize such aberrations, for example by adding additional compensatory elements which compensate for the aberrations. Slope error is a random error which cannot be reduced using such design optimization, as additional optical elements will only increase the slope error.

The issue of slope error is exacerbated when the measurement radiation is higher frequency than that of visible radiation, for example in the soft X-ray regime. The slope error is a particular problem in the soft X-ray regime because surface flatness (a surface accuracy specification which measures the deviation of a flat surface from true flat) of an optical surface is described in terms of wavelength $\lambda$ of the radiation incident on the surface. In the visible regime, optical elements with a surface flatness in the region of $\lambda/40$ is readily available. But with a wavelength in the region of 2 orders of magnitude smaller (e.g., in the region of 5 nm), it becomes much more difficult to achieve comparable surface flatness.

It is proposed to address the issue of slope error by spatially modulating the measurement radiation beam, to compensate for the slope error of the optical surface(s) directing and focusing the measurement radiation on the substrate. In an embodiment, the spatial modulation will modulate the wavefront of the measurement radiation to compensate for wavefront errors imposed by these optical surface(s).

In a first embodiment illustrated in FIG. 3(a), the spatial modulation is provided directly in the measurement radiation beam of an inspection apparatus. In such an embodiment, the spatial modulation may be provided anywhere in the measurement beam's path. By way of specific example, spatial modulation may be provided at a parallel propagating portion of the measurement beam's path, using for example a compensatory optical device 50. Regardless of its location in the beam path, the compensatory optical device 50 may comprise a spatial light modulation (SLM) device.

Figure 4:
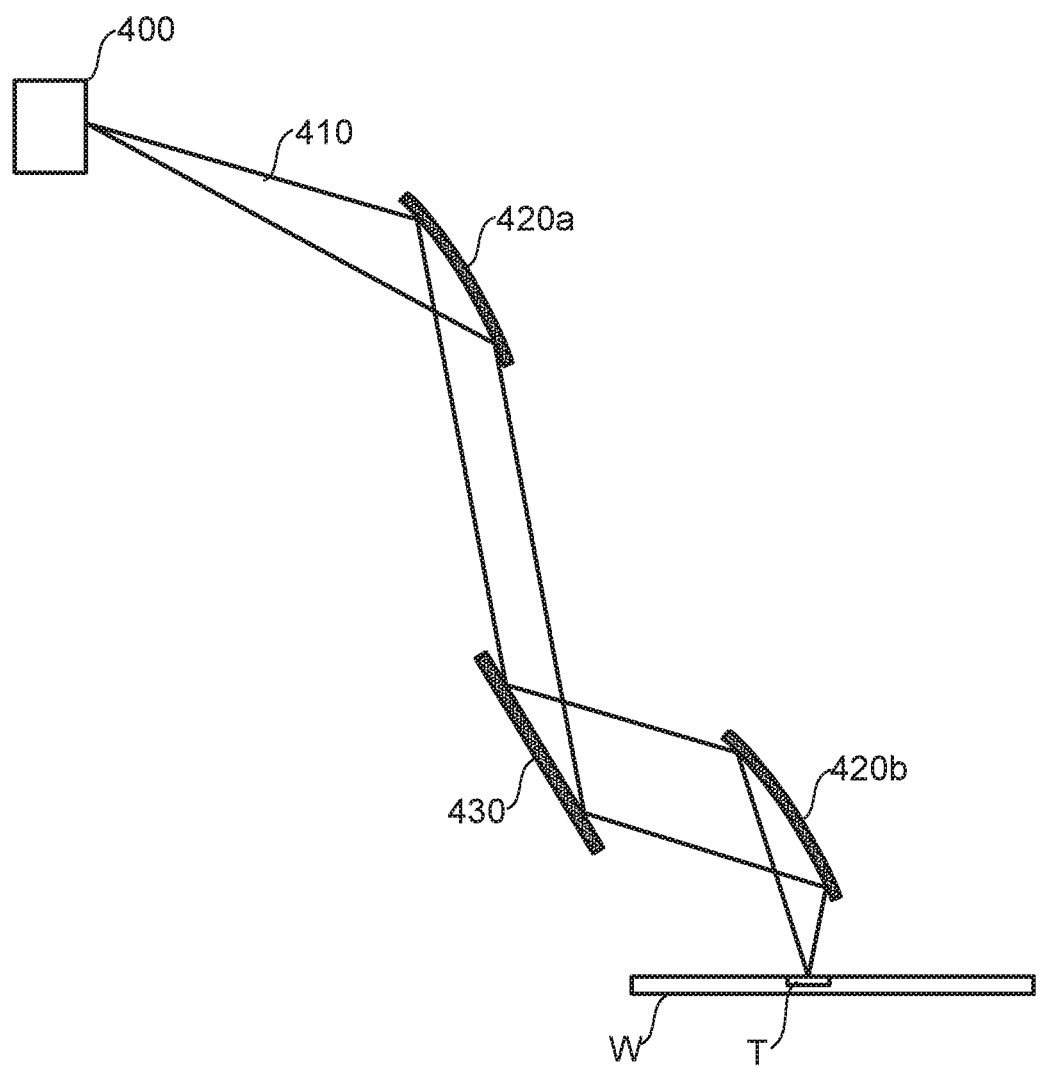
FIG. 4 schematically illustrates an illumination arrangement for a metrology apparatus according to an embodiment of the invention.

FIG. 4 shows a detail of a reflective arrangement for delivering measurement radiation to the target. FIG. 3(a) shows a transmissive compensatory optical device 50, mainly for drawing clarity. While such a transmissive compensatory optical device 50 is within the scope of this disclosure, it is more likely that the compensatory optical device is reflective. In particular, this is necessary when the measurement radiation comprises soft X-ray radiation.

FIG. 4 shows a radiation source 400 which provides measurement radiation 410, and optical elements 420a, 420b, for directing and focusing the measurement radiation 410 onto a target structure T on the substrate W. Also shown is a compensatory optical device 430, such as a spatial light modulation device (SLM), which provides a compensatory wavefront distortion to radiation which is incident on the compensatory optical device 430, which compensates for the wavefront distortion (slope error) imparted by optical element 420b and/or optical element 420a. The SLM device may be any suitable device which spatially modulates incoming radiation. By way of example, an SLM device may comprise:

- a deformable mirror—e.g., a piezoelectric deformable mirror which may comprise a plurality of piezo-actuators attached to the mirror backside. However, this may result in a large pitch such that their control is limited.
- a digital micromirror device (DMD)—Such devices are widely used and rugged. Using small pixels also enables fine control. However, such devices comprise a binary (on/off) system: if a pixel is 'off' it will not reflect any light through the system and the amount of light propagated will be reduced. This is not the case with the deformable mirrors, in which case the phase is adjusted. Also mirrors are flipped to be turned 'on' or 'off', typically over a +/−12 degrees range. In a grazing incidence regime, this could mean the shadow of one pixel is cast over a next pixel.
- A microelectromechanical system (MEMS) based deformable mirror. These are standard elements with a typical pitch of about 300-400 µm. As the typical spatial frequency for a slope error is approximately 1 mm, a pitch below this value makes fine control possible. Also sub-nm height steps are possible.

When the measurement radiation is high energy/soft X-ray radiation, it may be that the SLM device may require a special reflective coating such as, for example, iridium, ruthenium or gold. The SLM device should also be adapted and sized for grazing incidence (e.g. approximately 15 degrees with respect to the surface).

Figure 5:
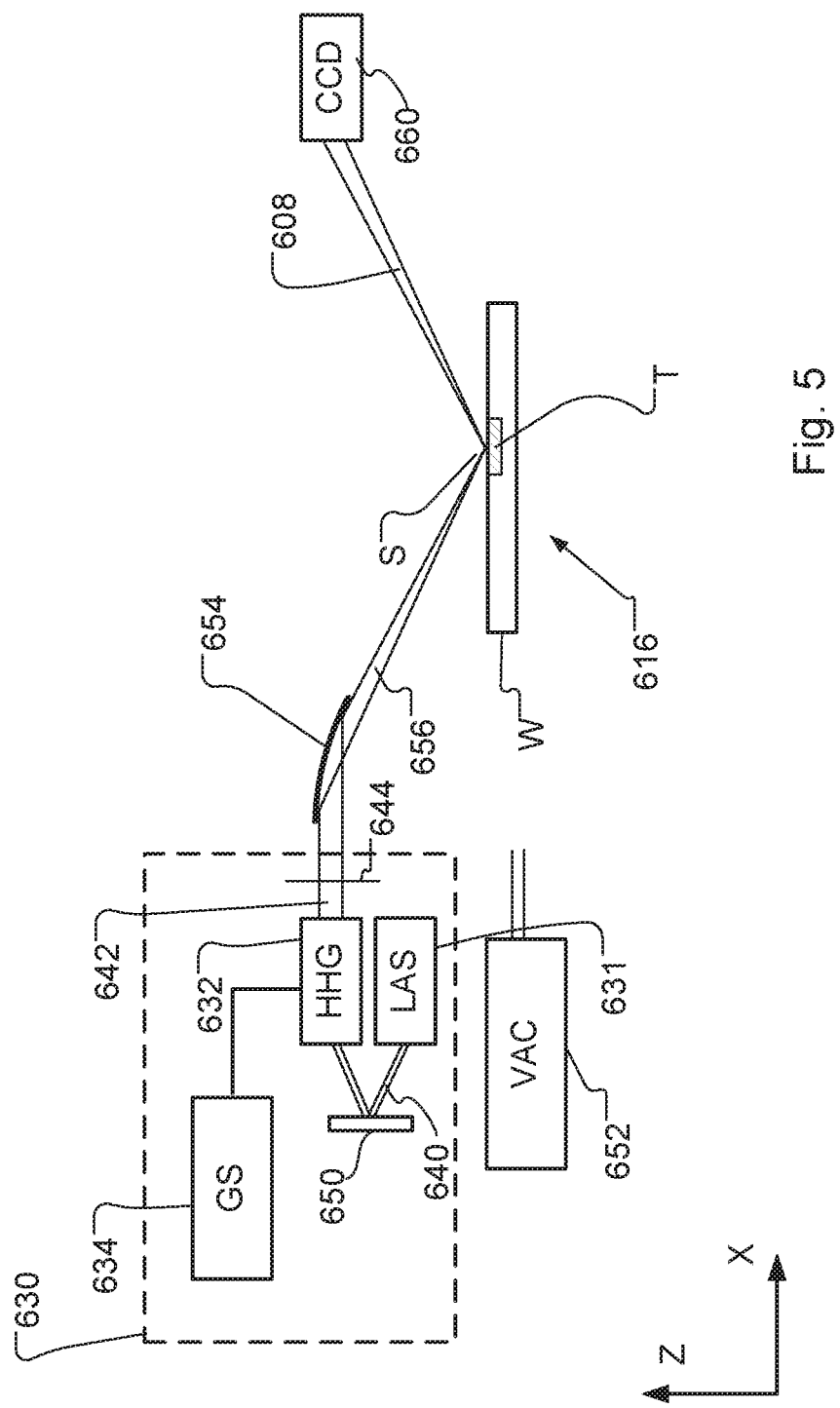
FIG. 5 schematically illustrates a metrology apparatus using a HHG source according to a first embodiment of the invention.

FIG. 5 illustrates a radiation source 630 and measurement arrangement according to an alternative embodiment. Radiation source 630 in the example of FIG. 5 is an HHG source for generating EUV radiation based on high harmonic generation (HHG) techniques. Main components of the radiation source 630 are a pump laser 631 and an HHG medium, such as a HHG gas cell 632. Other HHG media may equally be used, for example a solid surface medium or HHG gas within a hollow fiber. A gas supply 634 supplies suitable gas to the gas cell 632, where it is optionally ionized by an electric source t shown). The pump laser 631 may be for example a fiber-based laser with an optical amplifier, producing pulses of infrared radiation lasting less than 1 ns (1 nanosecond) per pulse, with a pulse repetition rate up to several megahertz, as required. The wavelength may be for example in the region of 1 µm (1 micron). The laser pulses are delivered as a pump (IR laser) radiation beam 640, via a compensatory optical device 650 to the HHG gas cell 632, where a portion of the radiation is converted to higher frequencies (up to frequencies in the EUV and/or soft X-ray regime). From the HHG gas cell 632 emerges a beam of measurement radiation 642 including coherent radiation of the desired wavelength or wavelengths.

In this embodiment, the compensatory optical device 650 no longer modulates the measurement radiation directly, but instead modulates the first laser) radiation beam 640, which then excites the HHG gas cell 632 to generate the measurement radiation 642. One property of HHG generation is that, due to the nature of the generation process, characteristics of the pump radiation beam 640 are carried over and copied into the generated HHG radiation beam 642. One such property is the wavefront shape. Consequently, spatial modulation of the pump radiation beam 640 will result in an equivalent spatial modulation of the generated measurement radiation 642.

An advantage of performing the modulation to the laser radiation is that there is a greater flexibility in the optical components which can be used for the compensatory optical device 650 when modulating infra-red radiation compared to soft X-ray radiation. The compensatory optical device 650 may be any of the SLIM devices already mentioned above in relation to the previous embodiment. However, the compensatory optical device 650 does not need to be specially adapted for X-ray radiation, and can use more conventional liquid crystal technology SLMs, for example. Also, a grazing angle of incidence is no longer necessary; the angle of incidence may instead be much closer to normal, as shown, which again allows the use of more conventional and smaller SLMs, and a simpler implementation. A transmissive compensatory optical device is also possible. A further advantage is that there is now no compensatory optical device modulating the soft X-ray measurement radiation. Since every optical device in the soft X-ray regime results in an additional slope error, having fewer optical elements in the soft X-ray regime is expected to improve results. Also, the compensatory optical device does not need to operate in the vacuum of the inspection chamber, which saves additional complexity.

It is important that the pump radiation beam 640 is properly focused on the HHG gas cell 632 to generate HHG radiation. It can be shown that the typical slope error being corrected for is small (for example, in the order of 10 s of microradian per mm), and therefore the compensatory modulation need only be small. As such, any defocusing of the pump radiation beam 640 by the compensatory modulation should not significantly affect HHG generation.

The measurement radiation 642 may contain multiple wavelengths. If the radiation is also monochromatic, then measurement calculations (reconstruction) may be simplified, but it is easier with HHG to produce radiation with several wavelengths. These are matters of design choice, and may even be selectable options within the same apparatus.

Different wavelengths will, for example, provide different levels of contrast when imaging structure of different materials. For inspection of metal structures or silicon structures, for example, different wavelengths may be selected to those used for imaging features of (carbon-based) resist, or for detecting contamination of such different materials. One or more filtering devices 644 may be provided. For example a filter such as a thin membrane of Aluminum (Al) may serve to cut the fundamental IR radiation from passing further into the inspection apparatus. Since the fundamental IR radiation and the emitted radiation (SXR beam) are collinear, the driving radiation typically needs to be blocked to prevent it passing through the radiation output and entering the vacuum optical system.

A grating may be provided to select one or more specific harmonic wavelengths from among those generated in the gas cell 632. Some or all of the beam path may be contained within a vacuum environment, bearing in mind that EUV radiation is absorbed when traveling in air. The various components of radiation source 630 and illumination optics can be adjustable to implement different metrology 'recipes' within the same apparatus. For example different wavelengths and/or polarization can be made selectable.

From the radiation source 630, the filtered beam enters an inspection chamber where the substrate W including a structure of interest or target structure is held for inspection by substrate support 616. The target structure is labeled T. The atmosphere within inspection chamber is maintained near vacuum by vacuum pump 652, so that the soft X-ray radiation can pass without undue attenuation through the atmosphere. The illumination system includes one or more optical elements 654 for focusing the radiation into a focused beam 656, and may comprise for example a two-dimensionally curved mirror, or a series (e.g., a pair) of one-dimensionally curved mirrors, as described in the prior applications mentioned above. It is the slope error of these optical element(s) 654 which is compensated for by the compensatory optical device 650. Diffraction gratings such as the spectroscopic gratings can be combined with such mirrors, if desired. The focusing is performed to achieve a round or elliptical spot under 10 μm in diameter, when projected onto the structure of interest. Substrate support 616 comprises for example an X-Y translation stage and a rotation stage, by which any part of the substrate W can be brought to the focal point of beam to in a desired orientation. Thus the radiation spot S is formed on the structure of interest. The radiation scattered 608 from the structure of interest is then detected by detector 660.

In all embodiments described above, it is envisaged that the compensatory optical device 50, 430, 650 may be tuned in a calibration step. Such a calibration step may optimize the wavefront correction to the slope error of the illumination system optical element(s) and therefore minimize blurring of the measurement spot. In an embodiment, this may be done by replacing the substrate W with a measuring device which measures the spot size, and adjusting the compensatory optical device 50, 430, 650 until the spot size is minimized. Optionally, the slope error of the optical element(s) of the illumination system may be measured and this measurement used to determine an initial starting configuration for the compensatory optical device 50, 430, 650 in the calibration step.

Because the spot size is typically smaller than the size of a single pixel of a detector it may be that it cannot simply be measured on a static CCD image. Instead, the spot may be measured by fully imaging the spot using e.g. a Schwarzschild objective and a CCD, using a pinhole of (approximately) the size of the illumination spot, or use a knife-edge method.

It is envisaged that such a calibration step is a one-time calibration: once the compensatory optical device is configured, it is not expected to require further adjustment. The slope error on the mirrors may be assumed (in an embodiment) to be a random, but static error. In an embodiment, the calibration step may be performed only once during construction. In other embodiments, the calibration step may have to be repeated periodically, although the timescale between successive calibrations should be weeks or longer. As such, no real-time, closed-loop control is needed, as can be found in many systems including a SLM. In other embodiments, more frequent recalibrations may be performed to capture a dynamic component of the slope error e.g., due to environmental effects, which may include thermal deformation and mirror surface contamination.

In a further alternative which better captures and corrects for any dynamic component, the spot size may be measured in real time (e.g., during production/substrate inspection) using a separate detector (e.g., located above and looking down on the substrate) and used in a feedback control loop to control the compensatory optical device 50, 430, 650 so as to minimize and/or optimize the spot size.

Because the NA of the illumination paths proposed for metrology is relatively low (Below 0.1), if the SLM is positioned in a parallel propagating part of the beam, the required wave front modulation changes only very gradually with the position of the SLM. This makes the proposal robust for small variations in the relative positions of the compensatory optical device and illumination optical element(s). As such, no complex spot size monitoring and feedback system is required during measurement; all subsequent measurements can then be performed using the compensatory optical device configuration determined in the calibration step.

The embodiment described in relation to FIG. 5, where the compensatory optical device 650 is located between the pump laser 631 and the HHG gas cell 632 so as to modulate the pump radiation beam 640, has greater applicability than the slope error compensation described up to now. A number of other applications for such an arrangement will now be described.

In a first such application, the compensatory optical device 650 may be used as part of a control loop to control positioning of the measurement radiation beam 656 on the target T. Due to small changes in the environment (e.g., to temperature and/or pressure), the focus position of the pump radiation beam 640 in the HHG gas cell 632 can drift. This effect is known as the pointing error or position error of the HHG source point (focused point of the measurement radiation beam 656). This induces a drift in the position of the measurement radiation beam 656 on the target. This is problematic, as the spot should remain properly focused at the target.

Figure 6:
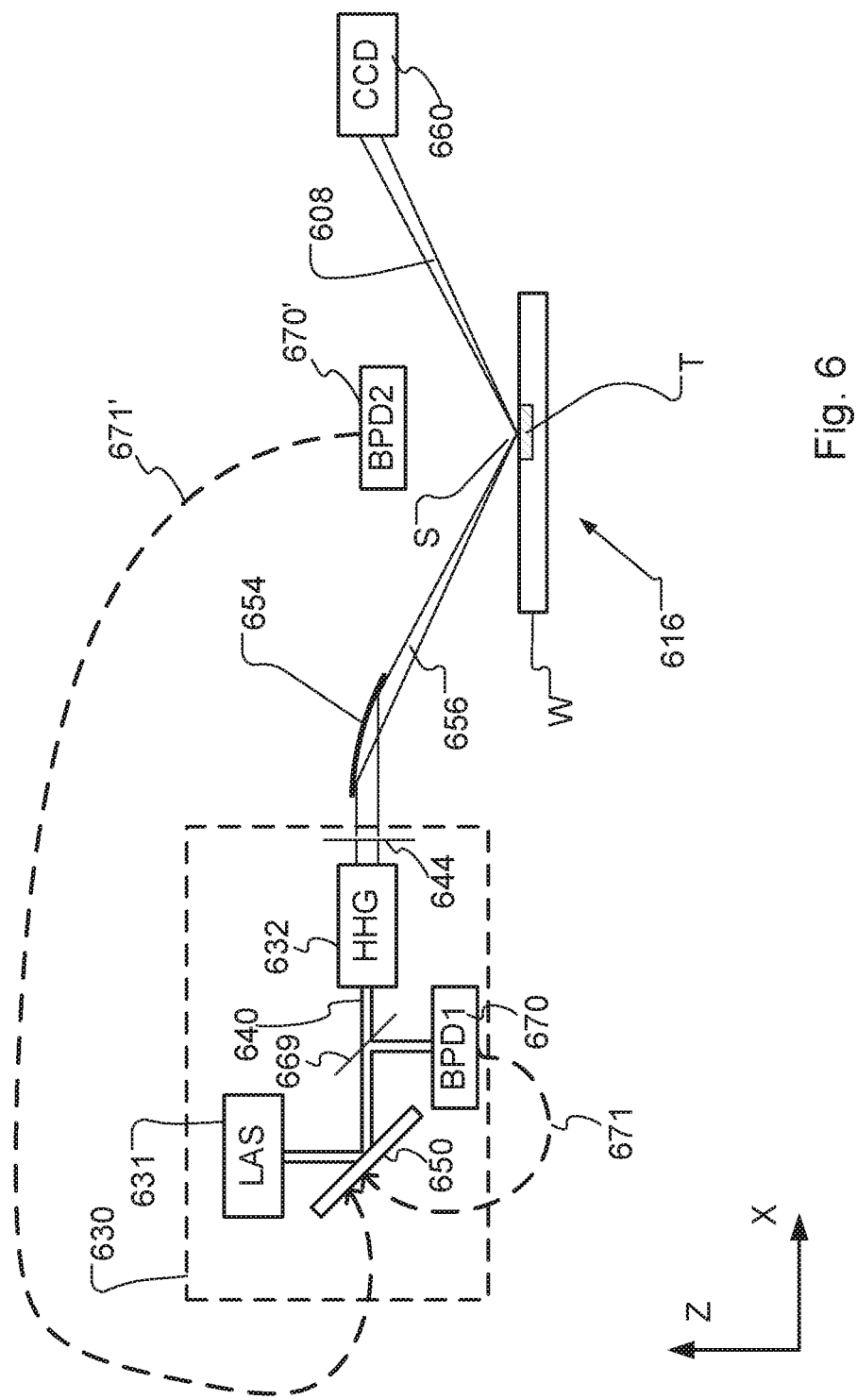
FIG. 6 schematically illustrates a metrology apparatus using a HHG source according to a second embodiment of the invention.

FIG. 6 illustrates two alternative arrangements for implementing such a control loop, a first arrangement which corrects for the pointing error directly by measuring the position of the beam of measurement radiation 656, and a second arrangement which corrects for the pointing error indirectly by measuring the position of the pump radiation beam 640 in the HHG cell 632. FIG. 6 shows a simplified depiction of the arrangement of FIG. 5. Though depicted in a simplified manner (for clarity) the only differences with the FIG. 5 arrangement is the provision of a beam position detector 670, 670' and control loop (depicted by arrows 671, 671') to control the compensatory optical device (or devices) 650 in order to correct for the pointing error. In this figure, two (alternative) options are shown for the beam position detector 670, 670'. It is envisaged that an actual arrangement will comprise only one of these alternatives; i.e., only beam position detector 670 (BPD1) and control loop 671 or beam position detector 670' (BPD2) and control loop 670'.

Considering first the beam position detector 670 (BPD1) embodiment, subsequent to the laser radiation beam 640 being reflected from (or transmitted through) the compensatory optical device 650, a small fraction of the pump radiation beam 640 is directed (by beam-splitter 669) to be sampled and measured by a beam position detector 670. The measured beam position of the pump radiation beam 640 is used as feedback information for the compensatory optical device 650 as indicated by arrow 671.

In the second beam position detector 670' (BPD2) embodiment, the measurement radiation beam 656 spot position is measured at the target T. As before, this measurement is fed back to the compensatory optical device 650 (as indicated by arrow 671') for control.

In either embodiment, a correction can be calculated which corrects for any pointing error (deviation of the measured beam position from a desired position). This correction may be implemented using the compensatory optical device 650 to add a wavefront modulation to the pump radiation beam 640 which results in a reduction or elimination of the pointing error.

In each case, the beam position detector 670, 670' may comprise, for example, a camera, quadrant photo detector (QPD), or a position sensitive detector (PSD). Such an embodiment may be implemented in combination with a spot size measurement as described above for slope error compensation. Both spot size and beam position may be measured, and corrections for the compensatory optical device 650 determined, so as to co-optimize and control both spot size and beam position. Where the beam position detector 670' is located to measure the position of the measurement radiation beam 656 on the substrate, the same beam position detector 670' could also be used to measure the spot size.

Implementing both detectors 670, 670' is not required; the preferred position will depend on certain design considerations, for example:

The positional information measured at the substrate (i.e., using BPD2 670') will be more accurate than measured at the BPD1 position; however it is easier to implement detection of the infra-red pump radiation beam 640 than the SXR measurement radiation beam 656.

If the pointing error is predominately or completely due to the pump laser 631, compensation using the information measured at the BPD1 670 position is quite feasible;

On the other hand, if the error in the spot position is dominated or significantly impacted by the position of e.g., the SXR optics (e.g., optical element(s) 654), measurement at the substrate (BPD2 670') is preferable.

Figure 7:
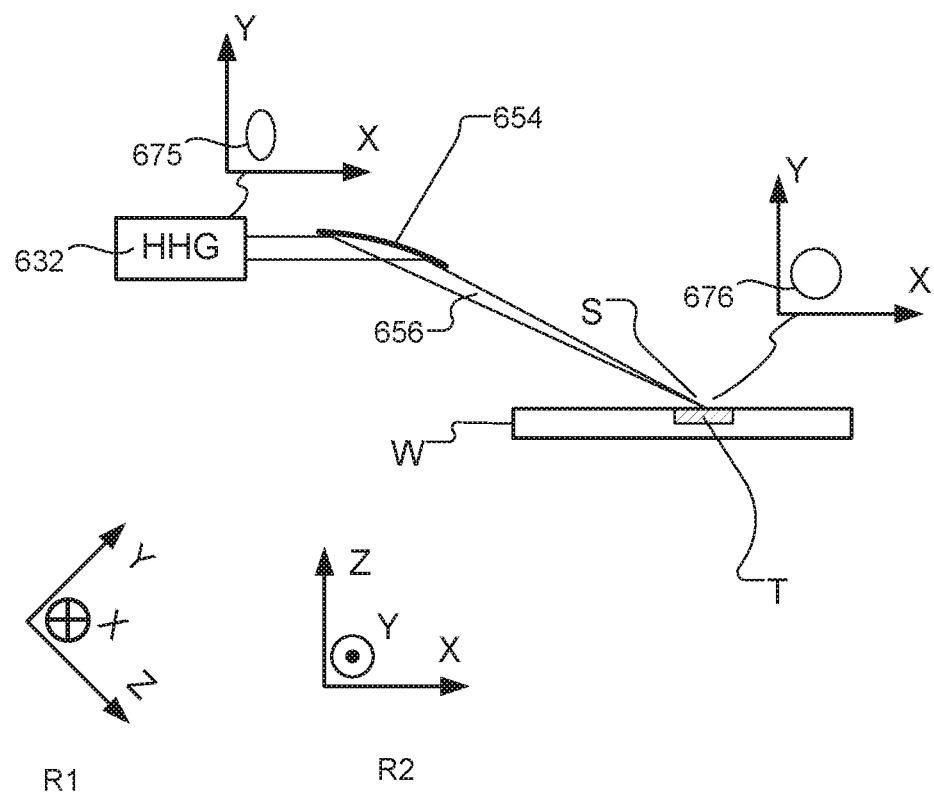
FIG. 7 schematically illustrates a detail of a metrology apparatus using a HHG source according to a further embodiment of the invention.

A second application for modulating the pump radiation beam 640, is to shape the pump radiation beam 640 to create an anamorphic measurement radiation beam 656. Such an application is described in relation to FIG. 7, which shows the measurement radiation beam 656 being delivered from the HHG gas cell 632 to the target T.

For applications such as CD reconstruction, the measurement radiation beam 656 is required to be at a grazing incidence angle relative to the target T. On the target T, a circular spot 676 is often desired. Therefore, the two principal axes X and Y require a very different magnification, due to the mismatch in the beam reference frame R1 of the beam at the HHG gas cell 632 and the substrate reference frame R2. Furthermore, overall system performance (especially in terms of the spot to target performance) may benefit from a non-circular symmetric beam profile. This holds for any configuration, and therefore may be applicable for near-normal incidence OVL measurements.

In order to achieve a required beam shape 676 at substrate level via the optical system 654 depicted, the optical system 654 would have to be fully anamorphic. Depending on the incidence angle, this may require treating the X and Y axes of the beam completely separately which doubles the number of components in the beam (X and Y would need separate, 1D curved sets of grazing incidence mirrors). This can be undesirable for a number of reasons which include:

Optics in this regime will be expensive;

Optics will be large in the z-direction of the beam (e.g., 200 mm), inducing volume conflicts if many such elements are required in the beam path;

Surface quality of the optical elements is relatively poor in this regime: every reflection reduces the beam quality.

If, however, the shape of the pump laser radiation spot at the HHG gas cell 632 is not circular, but elliptical, an anamorphic optical system can be obviated. One way to create such an elliptical beam is by applying a wavefront modulation on the pump radiation beam 640 by using a compensatory optical device 650. The compensatory optical device 650 may comprise an SPM or a set of cylindrical lenses or mirrors. The advantage of using an SPM is its flexibility: if the angle between the substrate W and the beam 656 is changed, the spot shape 675 at the HHG gas cell 632 can be adjusted in such a way to maintain a required beam shape (and therefore a circular or other desired shape spot 676) on the target.

In another application, the modulation of the pump radiation beam 640 can be used to induce different illumination patterns for lensless imaging. In a lensless system, such as that illustrated in FIG. 5, there are no imaging optics between the sample (target T) and detector. Instead, a CCD 660 is used in order to record the intensity distribution of the scattered light directly. If the complete field (amplitude and phase) at the position of the detector 660 is known, an image can be reconstructed.

An optical detector, however, only detects the intensity (related to the amplitude) of the detected radiation. With no direct phase information present, diversity needs to be introduced. This can be achieved by, e.g., measuring the amplitude at different propagation distances along the scattered beam, illuminating the sample with different colors, etc. It is also possible to achieve diversity by applying different illumination patterns. Therefore, it is proposed to use the compensatory optical device 650 (e.g., SLM) to modulate the pump radiation beam 640 to generate these different illumination patterns. The advantages of this approach include:

The illumination pattern can be changed on a millisecond timescale; this is similar to the detector speed;

The illumination patterns are known exactly; this can help with reconstruction;

The illumination patterns can be optimized to a specific target structure T in order to optimize reconstruction. In this context, optimization may be in terms of any metric, e.g., time, accuracy.

The compensatory optical device 650 can also be used in beamshaping in order to induce a top-hat (or flat top) profile on the measurement radiation beam 656 for better focusing into a target. If no modulation is applied, the propagated pump radiation beam 640, and hence the measurement radiation beam 656, has a Gaussian intensity profile. In order to perform metrology, up to 99.99% of the measurement radiation should be focused onto a spot of 3-4 µm.

In order to achieve this with a Gaussian intensity profile, a large portion of the Gaussian tails would need to be included. A more favorable solution would be to impose a top-hat beam profile for the measurement radiation beam 656, properly focused into the desired spot size. A compensatory optical device 650, such as an SLM, can be used to create a top-hat profile in the pump radiation beam 640; this profile would then be mirrored in the measurement radiation beam 656.

All of the applications discussed herein which use a compensatory optical device 650 (such as an SLM) to modulate the pump radiation beam 640 can be implemented individually or in any combination of two or more. To simplify the optical path as much as possible, it may be beneficial if all the aforementioned applications disclosed herein (including slope error compensation) were implemented simultaneously, e.g., via a single compensatory optical device 650. Because the different wavefront modulations can be considered a linear superposition, the use of e.g., an SLM which imposes such a linear superposition makes this possible. Therefore the SLM may be controlled by a controller which calculates a suitable wavefront modulation based on a linear superposition of each of the required corrections for all (or a subset) of the applications and embodiments disclosed herein.

It should be noted that phase matching should be taken into account when determining the wavefront modulation. Over the interaction length in the HHG gas cell 632, phase matching between the pump radiation beam 640 and measurement radiation beam 656 is important so as to optimize the conversion efficiency from infra-red to SXR radiation. It should be appreciated that while conversion efficiency is important, of more relevance is how much SXR measurement radiation is actually focused in the correct spot rather than the total SXR measurement radiation generated.

Figure 8:
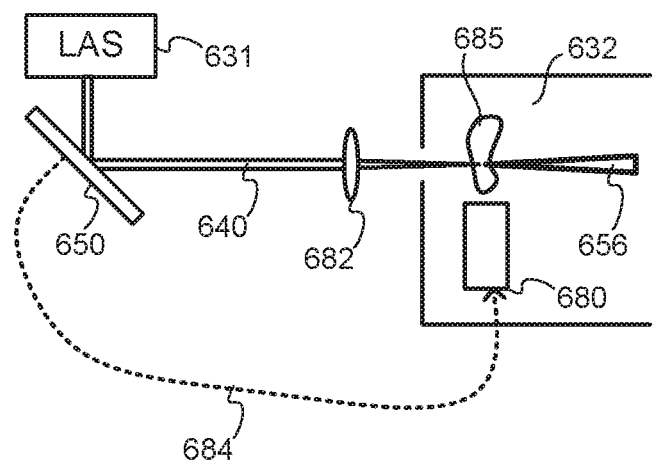
FIG. 8 schematically illustrates a detail of a HHG source according to an embodiment of the invention.

In order to improve phase matching with complex wavefronts, it is proposed that the gas density distribution within the HHG gas cell may be tuned. For example, the gas flow or gas speed can be modified. Also the gas supply may be designed in so as to tune the gas density distribution in order to meet the phase matching condition for a complex wavefront. If a proper calibration is executed, a feed-forward system could be used. Such a feed-forward system is conceptually illustrated in FIG. 8, which shows the pump radiation beam 640 from laser source 631 being focused, by focusing optics 682, onto a gas plume 685 within HHG gas cell 632 via the compensatory optical device 650 (e.g., SLM). A characteristic of the gas supply 680, for example gas speed and/or gas flow, may be altered thereby controlling the gas density distribution within gas plume 685, using a feed forward signal 684 to the gas supply 680. The feed forward signal 684 may be calculated based on the wavefront imposed by the compensatory optical device 650 (i.e., based on the programming of the compensatory optical device 650) so as to effect the phase matching.

Further embodiments are defined in the subsequent numbered clauses:

1. An inspection apparatus for measuring a target structure on a substrate, comprising:
   an illumination source for generating measurement radiation;
   an optical arrangement for focusing the measurement radiation onto said target structure, the optical arrangement comprising at least one optical element being arranged to receive said measurement radiation at a grazing incidence; and
   a compensatory optical device operable to spatially modulate the wavefront of the measurement radiation so as to compensate for a non-uniform manufacturing defect in said optical arrangement.

2. An inspection apparatus as in clause 1, wherein said non-uniform manufacturing defect in said optical arrangement comprises the slope error of at least one of said one or more optical elements of the optical arrangement.

3. An inspection apparatus as in clause 1 or 2, wherein said compensatory optical device comprises a spatial light modulation device.

4. An inspection apparatus as in clause 3, wherein the spatial light modulation device comprises one of a deformable mirror, a digital micromirror device, or a microelectromechanical system.

5. An inspection apparatus as in any preceding clause, comprising a measuring device at the substrate location operable to measure the size of a measurement spot resultant from the focusing of the measurement radiation.

6. An inspection apparatus as in clause 5, operable to perform an initial calibration step to configure the compensatory optical device so as to minimize the size of the measurement spot.

7. An inspection apparatus as in any preceding clause, wherein said measurement radiation comprises soft X-ray or Extreme Ultraviolet (EUV) radiation.

8. An inspection apparatus as in any preceding clause, wherein said compensatory optical device is located in a beam of said measurement radiation, so as to directly spatially modulate the wavefront of said beam of said measurement radiation.

9. An inspection apparatus as in clause 8, wherein said compensatory optical device is located in a parallel propagating portion of said beam of measurement radiation, between the illumination source and the substrate.

10. An inspection apparatus as in clause 9, wherein said compensatory optical device is located in a pupil plane of said inspection apparatus.

11. An inspection apparatus as in any of clauses 8 to 10, wherein said compensator optical device comprises a coating optimized for reflecting soft X-ray and/or Extreme Ultraviolet (EUV) radiation.

12. An inspection apparatus as in any of clauses 1 to 7, wherein:
   said illumination source is a high harmonic generation source comprising a high harmonic generation medium and a pump radiation source which emits pump radiation for exciting said high harmonic generation medium; and
   said compensatory optical device is operable to spatially modulate the wavefront of the pump radiation prior to it exciting said high harmonic generation medium, such that said spatial modulation of the wavefront of the pump radiation causes said spatial modulation of the wavefront of the measurement radiation.

13. An inspection apparatus as in clause 12, wherein said compensatory optical device is located in an optical path between the pump radiation source and high harmonic generation medium.

14. An inspection apparatus as in clause 12 or 13, wherein said pump radiation comprises infra-red radiation.

15. An illumination source for generating high harmonic radiation, comprising:
  a high harmonic generation medium;
  a pump radiation source which emits a beam of pump radiation for exciting said high harmonic generation medium to generate said high harmonic radiation; and
  a compensatory optical device operable to spatially modulate the wavefront of the beam of pump radiation prior to it exciting said high harmonic generation medium.

16. An illumination source as in clause 15, wherein said compensatory optical device is located in an optical path between the pump radiation source and high harmonic generation medium.

17. An illumination source as in clause 15 or 16, wherein said compensatory optical device comprises a spatial light modulation device.

18. An illumination source as in any of clauses 15 to 17, wherein the spatial light modulation device comprises one of a deformable mirror, a digital micromirror device, or a microelectromechanical system.

19. An illumination source as in any of clauses 15 to 18, wherein said pump radiation comprises infra-red radiation.

20. An illumination source as in any of clauses 15 to 19; wherein said compensatory optical device is operable to spatially modulate the wavefront of the beam of pump radiation so as to correct a position error of a beam of said high harmonic radiation.

21. An illumination source as in clause 20; being operable to:
  receive a position signal describing the position of a focused point of a beam wherein said beam is the beam of pump radiation or the beam of said high harmonic radiation;
  determine a correction for said position of the focused point of the beam relative to a desired position in terms of a wavefront modulation of the beam of pump radiation based on the position signal; and
  implement the correction via the compensatory optical device.

22. An illumination source as in clause 21, comprising a position detector being operable to measure said focused point of the beam so as to generate the position signal.

23. An illumination source as in clause 22, wherein the position detector is operable to measure the position of the focused point of the beam of pump radiation.

24. An illumination source as in clause 22, wherein the position detector is operable to measure the position of the focused point of the beam of high harmonic radiation.

25. An illumination source as in clause 24, wherein the position detector is further operable to measure the spot size of the focused point of the beam of high harmonic radiation and the illumination source is further operable to determine said correction to additionally minimize the spot size.

26. An illumination source as in any of clauses 15 to 25, wherein said compensatory optical device is operable to spatially modulate the wavefront of the beam of pump radiation so as to impart a desired profile on said beam of pump radiation, thereby imparting a corresponding profile on a beam of said high harmonic radiation.

27. An illumination source as in clause 26, wherein said desired profile comprises a non-circular cross-sectional profile on said beam of pump radiation.

28. An illumination source as in clause 27, wherein said non-circular cross-sectional profile comprises an elliptical cross-sectional profile, such that a beam of said high harmonic radiation generated by said illumination source forms a circular spot on a surface when focused at a grazing incidence on said surface.

29. An illumination source as in clause 26, 27 or 28, wherein said desired profile comprises a flat-top profile on said beam of pump radiation.

30. An illumination source as in any of clauses 15 to 29, wherein said compensatory optical device is operable to spatially modulate the wavefront of the beam of pump radiation so as to impart a varying illumination pattern on said beam of pump radiation.

31. An illumination source as in any of clauses 15 to 30, wherein high harmonic generation medium comprises a gas emitted by a gas source and the illumination source is operable to determine a feed forward control signal for control of the gas source so as to optimize phase matching between the beam of pump radiation and the generated high harmonic radiation, based on the spatial modulation of the wavefront of the beam of pump radiation imposed by the compensatory optical device.

32. An inspection apparatus for measuring a target structure on a substrate, comprising
  an illumination source as in any of clauses 15 to 31, for generating high harmonic radiation for measuring said target structure.

33. A method of measuring a target structure on a substrate comprising:
  spatially modulating the wavefront of measurement radiation to compensate for a non-uniform manufacturing defect in an optical arrangement comprising one or more optical elements;
  focusing the measurement radiation onto said target structure using said optical arrangement such that at least one optical element receives the measurement radiation at a grazing incidence, thereby illuminating the target structure with the measurement radiation;
  detecting scattered radiation resulting from the illumination of the target with the measurement radiation; and
  processing the detected scattered radiation to determine a measurement value relating to said target structure.

34. A method as in clause 33, wherein said non-uniform manufacturing defect in said optical arrangement comprises the slope error of at least one of said one or more optical elements of the optical arrangement.

35. A method as in clause 33 or 34, further comprising performing an initial calibration step comprising:
  measuring the size of a measurement spot resultant from the focusing of the measurement radiation; and
  configuring the spatial modulation so as to minimize the size of the measurement spot.

36. A method as in any of clauses 33 to 35, wherein said measurement radiation comprises soft X-ray or Extreme Ultraviolet (EUV) radiation.

37. A method as in any of clauses 33 to 36, wherein said step of spatially modulating the wavefront of measurement radiation comprises directly spatially modulating the wavefront of a beam of said measurement radiation.

38. A method as in clause 37, wherein said directly spatially modulating the wavefront of a beam of said measurement radiation comprises spatially modulating the wavefront of a parallel propagating portion of said beam of measurement radiation.

39. A method as in any of clauses 19 to 36 further comprising:
  generating said measurement radiation by exciting a high harmonic generation medium with pump radiation; and
  wherein said step of spatially modulating the wavefront of measurement radiation comprises spatially modulating the wavefront of the pump radiation prior to it exciting said high harmonic generation medium.

40. A method as in clause 39, wherein said pump radiation comprises infra-red radiation.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used in relation to the lithographic apparatus encompass all types of electromagnetic radiation, including ultraviolet (UV) radiation e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. An illumination source for generating high harmonic radiation, comprising:
   a high harmonic generation medium;
   a single pump radiation source configured to emit a single beam of pump radiation to excite the high harmonic generation medium to generate high harmonic radiation; and
   a compensatory optical device configured to spatially modulate a wavefront of the beam of pump radiation prior to it exciting the high harmonic generation medium,
   wherein the entire beam of pump radiation is spatially modulated by the compensatory optical device, such that the spatial modulation of the wavefront of the beam of pump radiation causes the spatial modulation of a wavefront of the high harmonic radiation.

2. The illumination source of claim 1, wherein the compensatory optical device is configured to spatially modulate the wavefront of the beam of pump radiation to correct a position error of a beam of the high harmonic radiation.

3. The illumination source of claim 2, wherein the compensatory optical device is configured to:
   receive a position signal describing the position of a focused point of a beam wherein the beam is the beam of pump radiation or the beam of the high harmonic radiation;
   determine a correction for the position of the focused point of the beam relative to a desired position in terms of a wavefront modulation of the beam of pump radiation based on the position signal; and
   implement the correction.

4. The illumination source of claim 3, further comprising a position detector configured to measure the focused point of the beam to generate the position signal.

5. The illumination source of claim 4, wherein the position detector is configured to measure the position of the focused point of the beam of pump radiation.

6. The illumination source of claim 4, wherein the position detector is configured to measure the position of the focused point of the beam of high harmonic radiation.

7. The illumination source of claim 6, wherein the position detector is further configured to measure a spot size of the focused point of the beam of high harmonic radiation and the compensatory optical device is further configured to determine the correction to additionally minimize the spot size.

8. The illumination source of claim 1, wherein the compensatory optical device is configured to spatially modulate the wavefront of the beam of pump radiation to impart a desired profile on the beam of pump radiation, thereby imparting a corresponding profile on a beam of the high harmonic radiation.

9. The illumination source of claim 1, wherein the compensatory optical device is transmissive.

10. The illumination source of claim 1, wherein the compensatory optical device is configured to co-optimize both a spot size of the high harmonic radiation and a beam position of the high harmonic radiation based on feedback information from one or more position detectors.

11. An illumination source for generating high harmonic radiation, comprising:
    a high harmonic generation medium;
    a single pump radiation source configured to emit a single beam of pump radiation to excite the high harmonic generation medium to generate high harmonic radiation; and a compensatory optical device configured to spatially modulate a wavefront of the beam of pump radiation prior to it exciting the high harmonic generation medium to compensate for a slope error due to manufacturing imperfections in one or more optical elements, wherein the compensatory optical device is configured to decrease the slope error and minimize a spot size of the high harmonic radiation.

12. The illumination source of claim 11, wherein the compensatory optical device is tuned in a calibration step and configured to optimize a wavefront correction to the slope error.

13. The illumination source of claim 11, wherein the slope error is measured and used to determine an initial configuration of the compensatory optical device.

* * * * *